United States Patent [19]

Sikorska et al.

[11] Patent Number: 5,264,556
[45] Date of Patent: Nov. 23, 1993

[54] MONOCLONAL ANTIBODIES FOR MEASURING OKADAIC ACID

[75] Inventors: Hanna Sikorska, Quebec, Canada; William S. Shestowsky, San Diego, Calif.

[73] Assignee: Rougier Inc., Montreal, Canada

[21] Appl. No.: 858,991

[22] Filed: Mar. 27, 1992

Related U.S. Application Data

[63] Continuation-in-part of Ser. No. 687,023, Apr. 18, 1991, abandoned.

[51] Int. Cl.$^5$ .............................................. C07K 15/00
[52] U.S. Cl. ................................ 530/387.2; 435/7.92; 435/7.93; 435/7.95; 436/548
[58] Field of Search ...................... 435/7.9, 7.92, 7.93, 435/7.95, 965; 436/548, 815, 822, 808; 530/387.1, 388.1, 387.2

[56] References Cited

U.S. PATENT DOCUMENTS 4,536,479  8/1985  Vander-Mallie .................. 436/537
4,699,880  10/1987  Goldstein ........................ 435/172.2

FOREIGN PATENT DOCUMENTS 0311456  4/1989  European Pat. Off. .

OTHER PUBLICATIONS

Uda, T. et al. "Enzyme Immunoassay Using Monoclonal Antibody Specific for Diarrhetic Shellfish Poisons", *Mycotoxins and Phycotoxins* '88 Elsevier Science Publishers B.V. Amsterdam, 1989, pp. 335–342.
Hokama, Y. et al. "Cross-Reactivity of Ciguatoxin, Okadais Acid, and Polyethers with Monoclonal Antibodies", *Food & Agricultural Immunology*, vol. 1 (1989) pp. 29–35.
Usagawa, T. et al. "Preparation of Monoclonal Antibodies Against Okadaic Acid Prepared from the Sponge Halichondria Okadai," *Toxicon* vol. 27, No. 12 (1989) pp. 1323–1330.

*Primary Examiner*—Esther L. Kepplinger
*Assistant Examiner*—Carol A. Spiegel
*Attorney, Agent, or Firm*—Cushman, Darby & Cushman

[57] ABSTRACT

The present invention relates to an anti-idiotypic monoclonal antibody raised against a mouse monoclonal antibody or fragments thereof specific to at least one diarrhetic shellfish poisoning toxin selected from the group consisting of okadaic acid and derivatives thereof. The anti-idiotypic antibody is characterized by reacting only with antibodies to okadaic acid and derivatives thereof but not with antibodies directed against any other compounds. The anti-idiotypic antibody is further characterized by being an internal image of okadaic acid and derivatives thereof. A hybridoma producing an anti-idiotypic antibody in accordance with the present invention has been deposited at the ATCC under accession number HB 10768. Competitive solid-phase assays for determining the amount of okadaic acid and derivatives thereof in marine samples are also provided in accordance with the present invention. The present invention also relates to a kit for determining the amount of okadaic acid and derivatives thereof in marine samples.

1 Claim, 6 Drawing Sheets

| R₁ | R₂ | |
|---|---|---|
| H | H | OKADAIC ACID (OA) |
| H | CH₃ | DINOPHYSISTOXIN-1 (DTX-1) |
| ACYL | CH₃ | DINOPHYSISTOXIN-3 (DTX-3) |

MONOCLONAL ANTIBODIES FOR MEASURING OKADAIC ACID

This application is a continuation-in-part of application Ser. No. 07/687,023 filed on Apr. 18, 1991, now abandoned.

BACKGROUND OF THE INVENTION

Okadaic acid is known to be a toxic $C_{38}$ polyether fatty acid first isolated from marine sponges *Halichondria okadaii*. Caused by enormous blooms of toxic phytoplankton known as "Red Tides", this toxin is produced and secreted by several types of marine dinoflagellates (plankton) of the genus *Dinophysis*. Okadaic acid accumulates in marine sponges, mussels, and scallops by filter feeding and has been implicated as the major component responsible for the phenomenon known as diarrhetic shellfish poisoning (DSP). DSP does not appear to be fatal, but its high morbidity rate and worldwide occurrence have made it a serious threat to the shellfish industry and to public health in general.

The first occurrence of diarrhetic shellfish poisoning was reported in the Tohoku District, Honshu Island, Japan, during the summer of 1976 and 1977. In the past decade, okadaic acid has been responsible for tens of thousands of human intoxications throughout Europe, South America, Hawaii, Chile, Indonesia, Japan, the United States and Canada. Between 1976 and 1985, the number of cases in Japan has exceeded 1300 despite the existence of extensive surveillance. In Spain alone as many as 5000 cases have been reported in 1981.

The dinoflagellate *Dinophysis acuminata* is probably responsible for okadaic acid production in most parts of Europe, while chemical analysis of the toxin isolated from *Dinophysis fortii* revealed the major component to be 35-methyl-okadaic acid. Accordingly, the compound was named dinophysis-toxin-1 (DTX-1)

In Norway, okadaic acid is found in mussels from the southern regions, while dinophysis-toxin-1 is found in mussels from the southwestern regions of the country. In both cases, *Dinophysis acuta* and *Dinophysis norwegica* are suspected of being responsible for the toxin infestation of the mussels.

The lethal potency of okadaic acid is 192 μg/kg when injected intraperitoneally in mice.

Recently, it has also became apparent that okadaic acid has potent tumor-promoting activity. It has been established that okadaic acid is capable of entering cells causing marked increases in the phosphorylation state of many proteins involved in the regulation of carbohydrate and lipid metabolism. Because protein phosphatases PP1 and PP2A are most probably the chief enzymes that reverse the actions of protein kinase C, it is not surprising that a potent phosphatase inhibitor (okadaic acid) should be as potent a tumor promoter as substances (phorbol esters) that activate protein kinase C. Tumor promotion presumably stems from increased phosphorylation of one or more proteins that are substrates for protein kinase C and dephosphorylated by PP1/PP2A.

No diarrhetic shellfish poisoning (DSP) standards to date are available in North America and no established assay exists for their detection. At present a number of countries, including Canada, Norway, Sweden, France and Japan are using suckling mice bioassays. However, this assay carries a considerable margin of error, is extremely tedious to perform and involves use of animals.

A group working on liquid chromatography assays was able to measure fluorescence intensity of the toxins after their reactions with 9-anthryldiazomethane (AGRIC. BIOL. CHEM., Lee S.S. et al., 1987, 51(3), pp.877–881). This method is sensitive but requires sophisticated, expensive equipment and highly skilled and trained personnel. It could never be adapted to field testing.

UBE Industries of Japan have recently introduced a new assay for measurement of okadaic acid (OA) in seafood samples. The assay, ELISA, is based on a competition between solid-phase bound okadaic acid and free okadaic acid for binding to anti-OA murine monoclonal antibody labelled with enzyme peroxidase (European Patent Application published on April 12, 1989 under No. EP-A-311,456).

The assay is very expensive due to the use of okadaic acid as a capture antigen. Okadaic acid is extracted from sponges, collection and processing of which is very expensive. The kit in the present form is not marketable for general, profilatic testing of seafood and plankton by fish industries due to its high cost and complicated sample preparation.

It would be highly desirable to have an assay for the measurement of okadaic acid which would be accurate, sensitive, easy to use and inexpensive.

SUMMMAY OF THE INVENTION

Surprisingly and in accordance with the present invention, there is provided an anti-idiotypic monoclonal antibody raised against a mouse monoclonal antibody specific to at least one diarrhetic shellfish poisoning toxin selected from the group consisting of okadaic acid and derivatives thereof, wherein the anti-idiotypic antibody is not immunoreactive with any non-anti-diarrhetic shellfish poisoning toxin antibody or fragments thereof, and wherein the anti-idiotypic antibody is an internal image of okadaic acid and derivatives thereof.

The anti-idiotypic antibody of the present invention can structurally and functionally mimic okadaic acid and derivatives thereof, whereby the anti-idiotypic antibody can act as a surrogate of okadaic acid and derivatives thereof.

There is also provided in accordance with the present invention, a competitive method for determining the amount of okadaic acid and derivatives thereof in a marine sample, which includes incubating at least a first mouse monoclonal antibody or fragments thereof specific to at least one diarrhetic shellfish poisoning toxin selected from the group consisting of okadaic acid and derivatives thereof, in parallel with an anti-idiotypic antibody raised against the first antibody, and an unknown amount of okadaic acid and derivatives thereof present in a marine sample, wherein at least one of said antibodies is solid-phase bound and wherein at least one of the antibodies is either enzyme labelled or indirectly detected, whereby the amount of okadaic acid and derivatives thereof in the sample is determined by comparing the extent to which it displaces the anti-idiotypic antibody from binding to the anti-diarrhetic shellfish poisoning toxin antibody with a calibration curve obtained with a known amount of okadaic acid or derivatives thereof There are also provided, in accordance with the present invention, several kits for determining the amount of okadaic acid and derivatives thereof in a marine sample which are adapted to be used according to the method of the present invention. A first kit of the present invention includes the following:

I) a solid surface having bound thereto a first mouse monoclonal antibody or fragments thereof specific to at least one diarrhetic shellfish poisoning toxin selected from the group consisting of okadaic acid and derivatives thereof;

II) a known amount of anti-idiotypic antibody raised against the first antibody or fragments thereof, enzyme labelled or indirectly detected; and III) a known amount of okadaic acid or derivatives thereof, whereby a standard curve is obtained.

A second kit of the present invention includes the following:

I) a solid surface having bound thereto an internal image anti-idiotypic antibody raised against an anti-okadaic acid antibody or fragments thereof;

II) a mouse monoclonal antibody or fragments thereof specific to at least one diarrhetic shellfish poisoning toxin selected from the group consisting of okadaic acid and derivatives thereof, which is enzyme labelled or indirectly detected; and III) a known amount of unlabelled anti-idiotypic antibody or fragments thereof, whereby a standard curve is obtained A third kit of the present invention includes the following:

I) a solid surface having bound thereto a mouse monoclonal antibody or fragments thereof specific to at least one diarrhetic shellfish poisoning toxin selected from the group consisting of okadaic acid and derivatives thereof;

II) a known amount of internal image antiidiotypic antibody or fragments thereof raised against an anti-okadaic acid antibody enzyme labelled or indirectly detected; and III) a known amount of unlabelled anti-idiotypic antibody or fragments thereof, whereby a standard curve is obtained.

A fourth kit of the present invention includes the following:

I) a solid surface having bound thereto an internal image anti-idiotypic antibody raised against an anti-okadaic acid antibody or fragments thereto;

II) a first mouse monoclonal antibody or fragments thereof specific to at least one diarrhetic shellfish- poisoning toxin selected from the group consisting of okadaic acid and derivatives thereof, which is enzyme labelled or indirectly detected; and III) a known amount of okadaic acid or derivatives thereof, whereby a standard curve is obtained.

Other advantages of the present invention will be readily illustrated by referring to the following description.

DETAILED DESCRIPTION OF THE INVENTION

Figure 1:
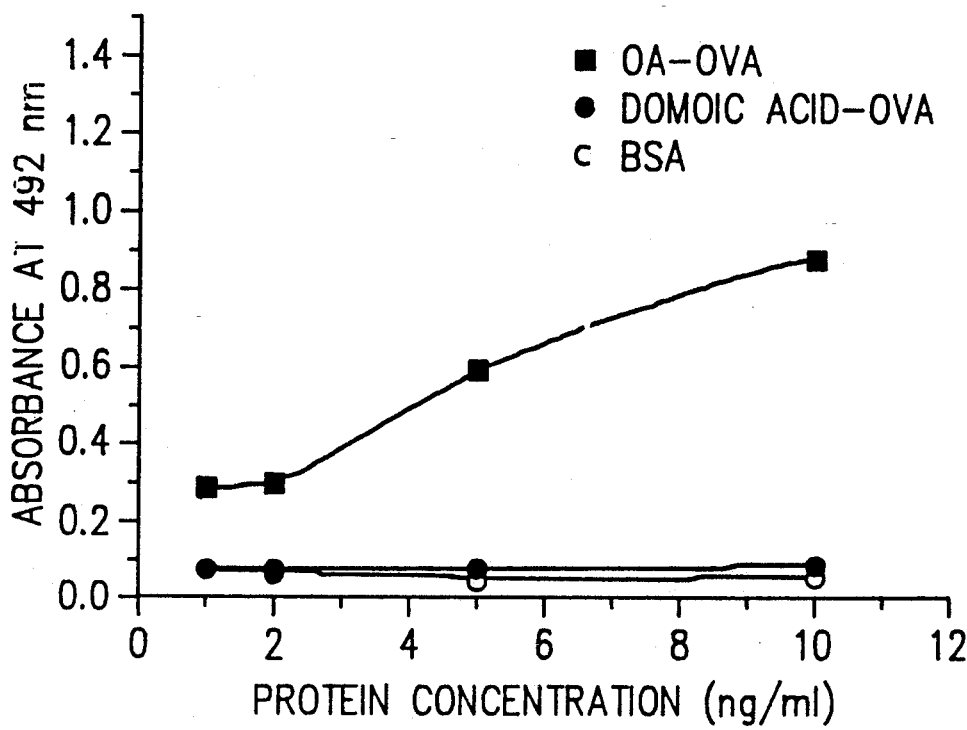
FIG. 1 shows a curve of the immunoreactivity of 6/50 monoclonal antibody towards different targets in ELISA.

Any animal injected with murine monoclonal antibody will develop antibodies against the immunoglobulin not only to Fc fragment but also to the antigen-binding site of the administered antibody Such antibodies are called anti-idiotypic antibodies, while the immunizing antigenic determinant located in or near the antigen-combining site of a given immunoglobulin molecule would be called idiotype Some of the generated anti-idiotypic antibodies would be directed against the antigen-binding site and others against framework sequences of the variable region. Some of the antigen-binding anti-idiotypic antibodies could mimic the original antigen, serving as an "internal image" of that antigen (ANN. IMMUNOL., Jerne N. K., 1974, 125C. pp.373-389). Those "internal image" anti-idiotypes could then act as antigens and lead to the production of anti-anti-anti-antibody (Ab$_3$) displaying similar or identical with Ab$_1$ antigen-binding characteristics. The generation and maintenance of such an idiotypic network is essential in immune system regulation.

Anti-idiotypic antibodies to hormone or hormone receptor antibodies have been shown to stimulate a physiological action of the ligand or exhibit receptor-like activities, such as binding the ligand or eliciting the production of anti-receptor antibodies when injected into animals. This has been found to be true for such ligands as insulin, retinol-binding protein, alprenolol, formylpeptide chemoattractant, thyroid-stimulating hormone (TSH), Bis Q, gp 70, acetylcholine, factor H, prolactin, substance P, and angiotensin II. Thus, for example, anti-idiotypic antibodies to anti-insulin antibodies were shown to interact with the membrane-bound insulin receptors and to mimic the action of insulin by stimulating the oxidation of glucose and its incorporation into lipids and by inhibiting lipolysis. Anti-idiotypic antibodies against an antibody to alprenolol, a potent antagonist of the β-adrenergic receptor, can stimulate adenylate cyclase. Anti-idiotypic antibodies to rat anti-human TSH antibodies mimic the biological activity of thyrotropin, in that they increase thyroid membrane adenylate cyclase activity, increase the rate of incorporation of $131_I$ into cultured thyrocytes, and organize these cells into follicles.

A monoclonal antibody to okadaic acid (6/50 IgG) was successfully selected, cloned and produced in accordance with the present invention. From a single animal immunized with 6/50 anti-okadaic acid antibody it was possible to select, not only an anti-idiotypic antibody to OA ($Ab_2$), but also an anti-anti-idiotypic antibody to OA ($Ab_3$). The selected anti-idiotypic antibody (1/59) reacted specifically only with F(ab')$_2$ fragments derived from the 6/50 IgG and did not react with either OA or F(ab')$_2$ fragments derived from pooled normal mouse serum IgG. To determine whether the 1/59 anti-idiotypic antibody binds to 6/50 IgG at the paratope (antigen-binding site), a series of competition ELISA assays were developed that showed that 1/59 IgG was indeed an internal image of okadaic acid that could mimic the physiological action of okadaic acid.

Okadaic acid can be isolated efficiently only from sponges. Purification process of okadaic acid is very tedious and expensive. Due to restricted supply of sponges and difficult purification process, okadaic acid is very expensive and not readily available.

Testing for seafood safety has to be inexpensive and simple to be affordable to fishermen and government regulatory agencies. Otherwise, the cost of seafood products to a consumer would be too high to absorb the cost of testing. It has to be underlined that okadaic acid is a strong tumor promoter and is thus undesirable as a contaminant of seafood.

As described above, an idiotypic antibody 1/59 that mimics functionally and structurally okadaic acid has been developed in accordance with the present invention. The solid-phase bound OA is replaced with solid-phase bound 1/59 and used in a competition ELISA assay for quantitation of okadaic acid.

The preferred kit of the present invention comprises either one Immulon ® 1 96-well microtiter plate or 8 strips consisting of 12 wells/strip. These plates or strips will have bound to their surface F(ab')$_2$ fragments derived from the anti-idiotypic monoclonal antibody 1/59 (10 μg/ml). Also supplied will be one bottle of lyophilized anti-okadaic acid mouse monoclonal antibody 6/50, one bottle of okadaic acid standard I (i.e. 9 ng/ml), one bottle of okadaic acid standard II (i.e. 27 ng/ml), one bottle of okadaic acid standard III (i.e. 81 ng/ml), one bottle of Tris-buffered saline, one bottle of Tween 20 ®, one package of powdered-milk, one bottle of enzyme labelled anti-mouse IgG anti-serum, one bottle of 3 N $H_2SO_4$ and enzyme substrate with instructions of preparation.

At least 25 different enzymes have been employed as labels in enzyme immunoassay (Table 1). Enzymes have a number of advantages over other types of label:

1. They are relatively cheap, are readily available in a purified form, and have a long shelf life.

2. A range of assays are available for measuring enzyme activity, and these can be performed on readily available equipment. Many of these assays can also be automated.

3. A single enzyme label can transform many molecules of substrate into product. This amplification effect provides the basis of very sensitive assays for enzymes 4 In cases where an enzyme label causes a loss of activity, indirect detection method would be preferable. An example of such method would be using enzyme labelled anti-sera.

TABLE I

| Examples |
|---|
| Oxidoreductases |
| Malate dehydrogenase |
| Glucose-6-phosphatase dehydrogenase |
| Glucose oxidase |
| Catalase |
| Horseradish peroxidase |
| Microperoxidase |
| Firefly luciferase |
| Bacterial luciferase |
| Transferases |
| Hexokinase |
| 6-Phosphofructokinase |
| Pyruvate kinase |
| Phosphoglucomutase |
| Ribonuclease A |
| Hydrolases |
| Acetylcholinesterase |
| Alkaline phosphatase |
| Phospholipase C |
| α-Amylase |
| Glucoamylase |
| Lysozyme |
| Glucosidase |
| β-Galactosidase |
| Invertase |
| Urease |
| Adenosine deaminase |
| Lyases |
| Carbonic anhydrase |
| Isomerases |
| 5,3-Ketosteroid isomerase |

The preferred enzyme used in the present invention is horseradish peroxidase.

The solid phase competitive method of the present invention has at least one antibody solid-phase bound. The solid support of this solid-phase assay can be selected from any one of the following: a microtitration plate, breakable strips (polyvinyl, polychloride, polystyrene, etc.), plastic beads, plastic tubes, latex particles, magnetic particles, nitrocellulose or acetate membranes and dipstick.

The expression "indirectly detected" refers to a second antibody, which recognizes a first antibody to be detected, wherein the second antibody is labelled and adapted to be used according to an assay of the present invention.

I. PRODUCTION OF ANTI-OKADAIC ACID MURINE MONOCLONAL ANTIBODY 6/50.

1. Preparation of Immunogen Conjugation of Okadaic Acid (OA) to Bovine Serum Albumin (BSA) and Chicken-Egg Ovalbumin (OVAL)

Okadaic acid is coupled to protein carriers BSA and OVAL using 1-ethyl-3-(3-dimethylaminopropyl) carbodiimice (EDC) and N-hydroxysulfosuccinimide (Sulfo-NHS ®, available from Pierce Chemicals) according to the method of Richardson et al. in J. UROL., Richardson et al., 1985, 54(1), p.186, with slight modifications. Okadaic acid, OVAL or BSA, EDC and Sulfo-NHS ® are dissolved in phosphate buffered saline (PBS, pH 7.4) at 4° C. in a ratio of 1:3:1:1, respectively. The Sulfo-NHS ® and EDC mediated reactions occur at physiological pH which insures the integrity of hapten-carrier conjugates.

In this reaction, okadaic acid is converted into an activated ester which become very efficient in binding either BSA or OVAL. To stop the reaction, the mixture dialyzed three times against phosphate buffered saline (PBS, pH 7.4), aliquoted, and stored at 20° C.

2. Immunization

To produce monoclonal antibodies to okadaic acid, six to eight week old female Balb/c mice are given initial subcutaneous (s.c.) inoculation of 2 µg of OA-BSA conjugate emulsified with an equal volume of complete Freund's adjuvant (Gibco Laboratories, Grand Island, N.Y.). All subsequent injections are made in incomplete Freund's adjuvant (1:1). At 4 weeks, they receive a second subcutaneous injection of 6 µg of OA-BSA, followed on the $7^{th}$ week by an identical third injection given intraperitoneally (i.p.). Two weeks later, mice with high sera titers as tested in enzyme-linked immunosorbent assay (ELISA) are boosted intraperitoneally with 5 µg of OA-BSA in PBS three days prior to fusion.

3. Fusion Procedure

Myeloma line P3X63,Ag8.653, known to be non-secretory is obtained from the American Type Culture Collection (ATCC). Prior to growing these cells in Dulbecco's Modified Eagle Medium (DMEM) supplemented with 10% fetal bovine serum (FBS), $2 \times 10^{-3}$M glutamine, $5 \times 10^{-2}$M 2-mercaptoethanol, and 0.001% gentamycin sulfate, they are grown for 1 week in the above medium containing $1 \times 10^{-4}$ 8-azaguanine to prevent any formation of revertant cells.

To ensure a high yield of hybrids, myeloma P3X63.Ag8.653 cells are kept in an exponential growth phase by replacing half the medium with fresh stock daily, for three days prior to fusion. Viable cells are enumerated by Trypan blue ® dye exclusion on the day of the fusion, and the cells used only if the viability exceeds 85% of total. The fusion protocol used has been described by Kohler et al. (NATURE, 1975, 256, p.495).

A single cell suspension of spleen cells is obtained by placing the spleens on a stainless steel mesh (grid no. 100) and flushing 5 to 10 ml of sterile Iscove's Modified Dubelcco's Medium (IMDM), containing only glutmine and gentamicin sulfate (fusion medium) at the concentration discussed above, through the spleen using a 10 ml syringe connected to a 25G needle. The myeloma and spleen cells are washed twice in fusion medium, enumerated, and mixed at a ratio of 1:5. The mixture is then centrifuged for 10 minutes at 1100 resolutions per minute (RPM) and the cell pellet is dislodged by gentle tapping of the tube. To the cell pellet, 1 ml of a 50% polyethylene glycol (PEG) Merck ® 4000 solution containing 5% dimethyl sulfoxide (DMSO) at pH 7.4 is then added dropwise over a period of 90 seconds while the tube is gently shaken. The mixture is agitated for another 30 seconds at which time 2 ml of fusion media are added dropwise for 90 seconds. Finally, the PEG solution is diluted by the addition of 20 ml of IMDM supplemented as described above for DMEM plus 1 mM sodium pyruvate, 0.1 mM non-essential amino acids and the mixture centrifuged at 180 g for 5 minutes. The pellet is resuspended in 10 ml of IMDM-10% FBS containing $1 \times 10^{-4}$M hypoxanthine, $4 \times 10^{-5}$M aminopterin, and $1.6 \times 10^{-5}$M thymidine or IMDM-HAT and the suspension placed in a 5% $CO_2$ incubator for 1 hour at 37° C. The cell con-centration is then adjusted to $10^6$ cells/ml and the cells distributed at $10^6$ cells/well in 24-well plates This is followed 4 days later by the addition of 1 ml IMDM-HAT/well.

Prior to screening, the medium is renewed three to four times in order to minimize false positives due to antibody secretion by short-lived activated B cells. This is achieved by removing one-half of the spent medium from each well and replacing it with an e-ual volume of fresh medium.

4. Selection of Hybrids

Supernatants are screened against OA-OVAL 14 to 21 days after the fusion when colonies are evident, by ELISA using peroxidase-conjugated antibodies. Briefly, 96-well Immulon ® 1 microtiter plates (Dynatech Laboratories) are coated with 10 µg/ml of OA-OVAL in 0.05 M sodium carbonate bicarbonate buffer, pH 9.6, overnight at 4° C. The unbound OA-OVAL is washed off with Tris-buffered saline (TS)-Polyoxyethylenesorbitan (Tween ®) and the remaining binding sites saturated with 1% powdered milk in TS for one hour at 37° C. After washing, the plates are incubated with the hybridoma supernatants for one hour at 37° C. After the unbound antibody is washed off, either a peroxidase-conjugated goat anti-mouse IgG (H+L) or a peroxidase-conjugated goat anti-mouse Fc fragment (Jackson Laboratories) is added and incubated for an additional 1 hour at 37° C. The colorimetric reaction is developed upon the addition of 0.03% $H_2O_2$ in 0.1M sodium citrate buffer, pH 7.0, containing 0.1% o-phenylenediamine dihydrochloride (OPD) (obtained from the Sigma Chemical Co. St-Louis, USA). The reaction is stopped with 3 N $H_2SO_4$ and the color intensity measured at a wavelength of 492 nm using a Bi-oRad ® ELISA reader (Bio-Rad, Mississauga, Ontario).

Hybridoma cultures that secrete anti-okadaic acid monoclonal antibodies are further expanded into 24-well plates. When confluency is reached each clone is subcloned at concentrations of 1 and 0.5 cells/well by the limiting dilution method into 96-well plates containing IMDM-$1 \times 10^{-4}$M hypoxanthine, $1.6 \times 10^{-5}$M thymidine (HT) medium over a feeder layer of murine spleen cells. Only wells containing single colonies are screened for specific antibody secretion in ELISA and then expanded gradually. Each clone of interest is then subcloned at least twice to ensure clonal stability. A clone designated 6/50 has been selected for further -haracterization since it secretes antibody with high affinity for OA.

5. Large Scale Production of 6/50 Monoclonal Antibody

Once an antibody secreting hybridoma has been successfully cloned, large amounts of the antibody are obtained by growing the hybridoma as a transplantable ascites tumor in male Balb/c mice. The mice are primed by an intraperitoneal (i.p.) injection of 0.5 ml of 2,6,10,14-tetramethylpentadecane (Pristane ®) (Sigma) two weeks prior to the injection of $5 \times 10^6$ cultured 6/50 hybridoma cells. An ascites usually develops within 2 weeks at which time the animals are sacrificed and the ascitic fluid collected from the peritoneum. The ascitic fluid is stored at −20° C. until further purification as described below.

6. Isolation of Immunoglobulin

The 6/50 antibodies are purified from ascites by affinity chromatography on Protein-A Sepharose ® (Pharmacia). Briefly, the collected ascites is first centrifuged at 3000 RPM for 15 minutes in order to remove any red blood cells as well as Pristane ® that might be present. The supernatant is then further centrifuged at 20,000 RPM for 1 hour to remove unwanted debris. The supernatant is then filtered through 0.45 μm membrane and further dialyzed against protein A binding buffer (1.45 M glycine, 3 M NaCl, pH 9.4) overnight at 4° C. A total of 120 mg of protein in 5 ml of binding buffer is loaded onto the column, washed and the IgG eluted with Bio-Rad ® protein A elution buffer (pH 3.1) at 1 ml/min.

Tne immunoglobulin containing fractions are pooled, neutralized with NaOH, dialyzed extensively against 3 changes of PBS (0.14 M NaCl, 2.7 mM KCl, 1.5 mM $KH_2PO_4$, 8.1 mM $Na_2HPO_4$), and concentrated by ultrafiltration on a PM30 ® membrane (Amicon). The immunoglooulin samples are then aliquoted and frozen at $-20°$ C. until used.

7. Determination of Immunoglobulin Subclass of 6/50 Antibody

The immunoglobulin isotype of 6/50 antibody is determined by double immunodiffusion in 1% agarose against monospecific, commercially available antimouse immunoglobulin class and subclass specific antisera. 6/50 antibody has been found to be $IgG_1\kappa$.

8. Determination of Isoelectric Point

The isoelectric point (pI) of 6/50 antibody is determined in Pharmacia's Phast Gel ® system in which pre-cut homogeneous polyacrylamide gels containing Pharmalyte ® carrier ampholytes in the 3 to 9 pH range are used. The pI of 6/50 IgG has been found to be at pH 5.85.

9. Preparation of F(ab')$_2$ Fragments of 6/50 IgG

F(ab')$_2$ fragments are prepared by limited proteolysis of 6/50 IgG with pepsin (Worthington, Freehold, N.J.). Due to the variation among individual monoclonal antibodies of each subclass with respect to digestion such parameters as optimal pH and incubation period are determined experimentally to obtain maximum yields. The course of digestion is monitored on an hourly basis by 12.5% sodium dodecyl sulfate polyacrylamide gel electrophoresis (SDS-PAGE) under both mercaptoethanol reducing and non-reducing conditions. Retention of antibody activity is evaluated in ELISA. Optimal conditions for preparation of F(ab')$_2$ fragments have been found to be a 24 hour digestion at pH 3.9 using a pepsin-IgG ratio of 1:50 in 0.1M sodium citrate buffer.

Unigested $IgG_1$ and Fc fragments are easily removed by passages through Protein A-Sepharose ® column. The purified 6/50-F(ab')$_2$ fragments still retain their activity towards okadaic acid in ELISA.

10. Immunoreactivity of 6/50 IqG

Immunologic specificity of 6/50 IgG has been determinec in ELISA as described above. Microtitration wells are coated with either OA-OVAL, OVAL, BSA or domoic acid and incubated with 6/50 IgG as described above. The 6/50 antibody reacts only with OA (FIG. 1).

The hybridoma producing the 6/50 antibody has been deposited at the American Type Culture Collection (ATCC, 12.301 Parklawn Drive, Rockville, Md. 20852 USA) on Jun. 6, 1991 under deposit number ATCC HB 10767. This deposit is available to be public upon the grant of a patent to the assignee, Rougier Inc., disclosing same. The deposit is also available as required by Foreign Patent laws in countries wherein counterpart applications are filed.

II. Production of a Mouse monoclonal Anti-idiotypic Antibody to a Mouse Anti-OA Monoclonal Antibody

1. Preparation of Immunogen

Conjugation of Anti-okadaic Acid Monoclonal Antibody (6/50) to Tuberculin Purified Protein Derivatives (PPD)

The anti-OA monoclonal antibody 6/50 is conjugated to PPD according to the method developed by Cambridge Research Biochemicals Ltd. (Cambridge, UK). Briefly, 5 μl of commercial high-grade glutaraldehyde (Sigma Chemical Co.) is added to a glass vial containing 10 mg of PPD dissolved in 920 μl of sodium hydrogen carbonate buffer (pH 8.4) and 2 mg of anti-OA monoclonal antibody 6/50 (mAb) prepared in 275 μl of the same buffer. The contents are stirred for 12 to 18 hours at room temperature. The final PPD concentration is 4 mg/ml. The conjugate is then dialyzed in the tubing provided, against two changes of 0.9% sodium chloride solution for 24 to 28 hours at 4° C. After dialysis, the conjugate is aliquoted and stored at $-20°$ C. until required for immunization.

2. Immunization

To produce anti-idiotypic monoclonal antibodies, Balb/c female mice are first inoculated s.c. with 25 μg bacillus Calmette-Guérin (BCG) vaccine three weeks prior to the first immunization with the anti-body-PPD conjugate. At week 3, 87 μg of the mAb-PPD conjugate in a 1:1 emulsion of incomplete Freund's adjuvant is administered s.c. On the seventh week, animals are inoculated s.c. with the same emulsion followed by another one on the tenth week given i p. Finally, two weeks later, mice with high sera titers are boosted i.p. with 5 μg of anti-okadaic acid mAb-PD in sterile PBS three days prior to fusion.

3. Fusion Procedure

Myeloma P3X63.Ag8.653 cells are fused with spleen cells from immunized mice in the presence of 50% PEG and 5% DMSO at pH 7.4 as described above for 6/50 IgG.

4. Selection of Hybrids Secreting Antibodies Against Anti-OA 6/50 IgG F(ab')$_2$ Hyoridoma supernatants are screened for antibody secretion in ELISA. Microtitration wells are coated with F(ab')$_2$ fragments of 6/50 IgG, and then incubated with culture supernatants collected from growing hybrids. Bound antibodies are detected with peroxidase anti-mouse immunoglobulin (Ig) Fc fragment-specific conjugate as described above (paragraph I.4).

Immunization of mice with syngeneic monoclonal antibody to OA results in the production of several hybridomas secreting anti-idiotypic antibodies (Ab2) reactive with 6/50 IgG as well as anti-OA antibodies (Ab3) induced through idiotypic cascade. One of Ab2 secreting hybridomas designated 1/59 was selected for propagation in culture. To insure its monoclonality and stability, it was subcloned by limiting-dilution as described above for 6/50 IgG.

5. Large-Scale Production of 1/59 Monoclonal Antibody

Large amounts of antibodies are obtained by growing 1/59 hybridoma as a transplantable ascites tumors in male Balb/c mice. The mice are primed by an i.p. injection of 0.5 ml of Pristane® two weeks prior to the injection of 5×106 cultured 1/59 hybridoma cells. An ascites usually develops within 2 weeks at which time the animals are sacrificed and the ascitic fluid collected from the peritoneum.

6. Isolation of Immunoglobulin 1/59

1/59 antibodies are purified from ascites by affinity chromatography on Protein-A Sepharose® (Pharmacia, Uppsala, Sweden). Briefly, the collected ascites is first centrifuged at 3000 RPM for 15 minutes in order to remove any red blood cells as well as Pristane® that may be present. The supernatant is then further centrifuged at 20,000 RPM for 1 hour to remove unwanted debris. The supernatant is then filtered through a 0.45 μm membrane (Millipore, Bedford, Mass.) and rurther dialyzed against protein A binding buffer (1.45 M glycine, 3 M NaCl, pH 9.4) overnight at 4° C. A total of 120 mg of protein in 5 ml of binding buffer is loaded onto the column, washed and the IgG eluted with Bio-Rad® protein A elution buffer (pH 3.1) at 1 ml/min. The immunoglobulin containing fractions are pooled, neutralized with NaOH, dialyzed extensively against 3 changes of PBS, and concentrated by ultrafiltration on a PM30® membrane. The immunoglobulin samples are then aliquoted and frozen at −20° C. until used.

7. 1/59 Immunoqlobulin Subclass Determination

The immunoglobulin isotype of 1/59 is determined by double immunodiffusion in 1% agarose against monospecific, commercially available anti-mouse immunoglobulin class and subclass specific antisera. The 1/59 μmmunoglobulin subclass has been found to be $IgG_1\kappa$.

8. F(ab')₂ Fragment Isolation From Anti-okadaic Acid Anti-idiotypic Antibody 1/59

Limited proteolysis of immunoglobulins with the enzyme pepsin is widely used for the preparation of F(ab')₂ fragments.

The 1/59 IgG at a concentration of 1 mg/ml is digested with pepsin at a ratio of 1:50 for 24 hours at 37° C. in 0.1 M sodium citrate buffer pH 3.9. The proteolysis is stopped by raising the pH to 8.0 with 1M Tris-HCl (pH 10.3).

Undigested IgG and Fc fragments are easily removed by passages through a Protein A-Sepharose® column. The purified 1/59 F(ab')₂ fragments still retained their activity to 6/50 IgG in ELISA.

9. Immunoreactivity of 1/59 IgG

Immunospecificity of 1/59 IgG has been tested in ELISA. Microtitration wells are coated with F(ab')₂ fragments of either 6/50 IgG (idiotype) or F(ab')₂ fragments of pooled normal mouse IgG and incubated with 1/59 IgG. Bound 1/59 antibody is detected with peroxidase conjugated anti-mouse IgG Fc fragment-specific as described previously.

The 1/59 anti-idiotypic antibody reacts only with F(ab')₂ fragments of 6/50 IgG.

Figure 2:
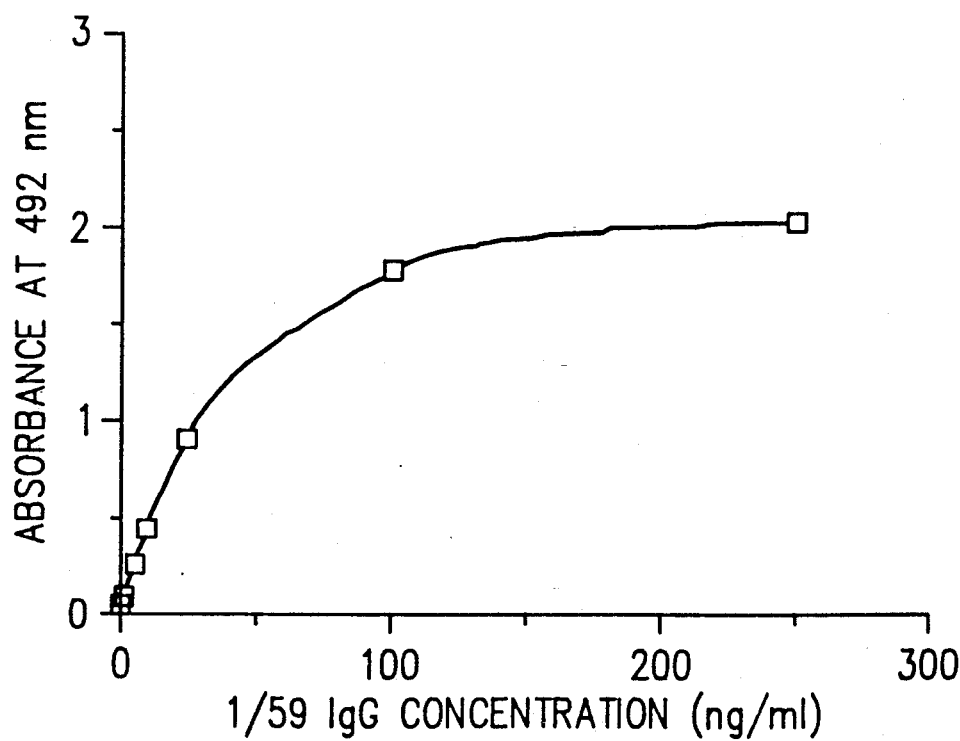
FIG. 2 shows a curve of the titration of 1/59 anti-idiotypic IgG against anti-OA 6/50 idiotype in ELSIA.

The 1/59 IgG titration curve against F(ab')₂ fragments of 6/50 IgG is presented in FIG. 2.

The hybridoma producing the 1/59 antibody has been deposited at the American Type Culture Collection (ATCC, 12301 Parklawn Drive, Rockville, MD 20852 USA) on June 6, 1991 under deposit number ATCC HB 10768. This deposit is available to be public upon the grant of a patent to the assignee, Rougier Inc., disclosing same. The deposit is also available as required by Foreign Patent laws in countries wherein counterpart applications are filed.

The present invention will be more readily understood by referring to the following examples which are given to illustrate the invention rather that to limit its scope.

EXAMPLE I

Competition Between Anti-idiotypic 1/59 IgG and OA For Binding to 6/50 Idiotype When OA is Fixed to a Solid-phase and 6/50 Measured in ELISA Briefly, microtitration plates are coated with 10 μg/ml of OA-OVAL and incubated simultaneously with increasing amounts of anti-idiotypic antibody 1/59 (0–10 μg/ml) and a fixed amount of 6/50 IgG (30 ng/ml) for 1 hour at 37° C. Bound 6/50 IgG is detected with peroxidase-anti-mouse IgG conjugate.

Figure 3:
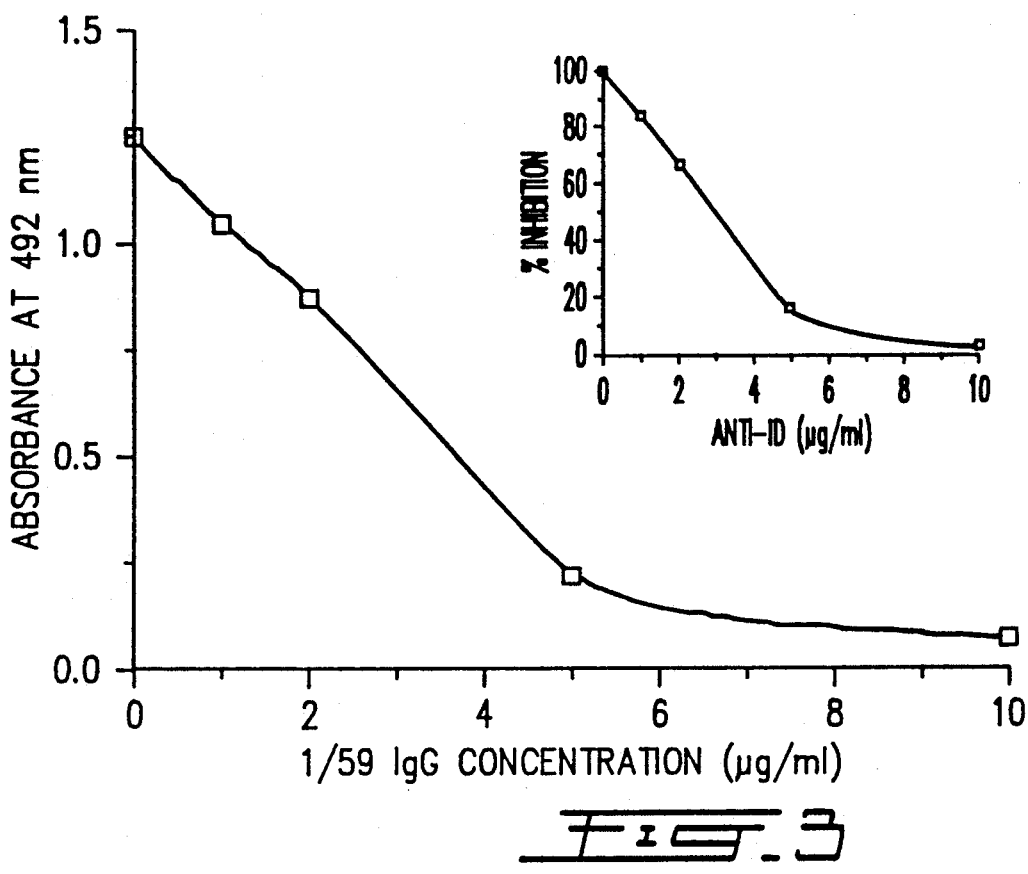
FIG. 3 shows a curve of the inhibition of anti-OA 6/50 IgG binding to okadaic acid by anti-OA anti-idiotypic 1/59 IgG in ELISA.

When free 1/59 IgG is competing with solid-phase bound OA for a limited number of binding sites on anti-OA 6/50 IgG, a marked decrease in bound 6/50 is observed. Thus, results presented in FIG. 3 indicate that 1/59 anti-idiotype binds to the same binding site on 6/50 idiotype as does the nominal antigen, OA.

EXAMPLE II

Competition Between Anti-idiotypic IgG 1/59 and Free OA for Binding to 6/50 IgG Fixed to a Solid-phase When Anti-idiotypic Antibody is Measured in ELISA.

In the reverse assay, 96-well microtiter plates are coated with 100 μl of 10 μg/ml of F(ab')₂ fragments of 6/50 IgG in 0.05M sodium carbonate bicarbonate buffer, pH 9.6, overnight at 4° C. The unbound F(ab')₂ fragments are washed off with Tris-buffered saline and the remaining binding sites are saturated with 200 μl of 1% powdered-milk in Tris-saline (TS-MILK) for one hour at 37° C. After washing, the wells are incubated simultaneously with 50 μl of a fixed amount of anti-idiotypic IgG 1/59 (500 ng/ml) and 50 μl of free OA diluted in 10% methanol (MeOH) at increasing concentrations (0–10 μg/ml) for one hour at 37° C. After the unbound antibody and antigen are washed off, 100 μl of a peroxidase conjugated goat anti-mouse IgG Fc-fragment-specific antiserum is added for one hour at 37° C.

The colorimetric reaction is developed upon the addition of 0.03% $H_2O_2$ in 0.1 M sodium citrate buffer, pH 7.0, containing 0.1% OPD. The reaction is stopped with 3 N $H_2SO_4$ and the color intensity measured at a wavelength of 492 nm using a BioRad® ELISA reader.

Figure 4:
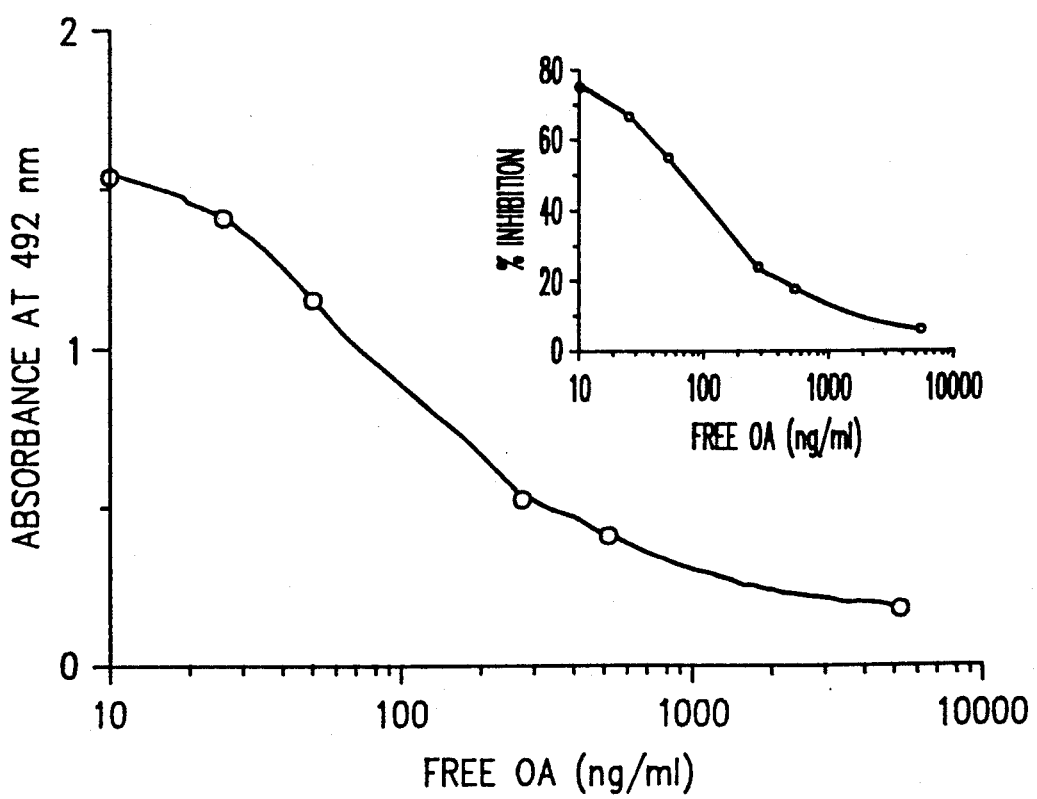
FIG. 4 shows a curve of the competition between anti-OA anti-idiotypic 1/59 IgG and free okadaic acid for binding to anti-OA 6/50 antibody in ELISA.

In this assay, free OA clearly inhibited the binding of anti-idiotypic 1/59 IgG to solid phase bound 6/50 IgG F(ab')₂. The results presented in FIG. 4 reconfirm the previous finding that OA and anti-idiotype compete for the same binding sites on the variable region of the 6/50 idiotype. Thus, we can conclude that 1/59 may represent an internal image of OA and thus function as a surrogate of the antigen in a competitive ELISA.

EXAMPLE III

Inhibition of Protein Phosphatase PP1/PP2A Catalytic Activity By an Internal Image Anti-okadaic Acid Anti-idiotypic Antibody.

The biological activity of OA was assayed by the ability of this toxin to inhibit dephosphorylation of $^{32}$P-radiolabelled glycogen phosphorylase (E.C. 2.4.1.1) by protein phosphatases (E.C. 3.1.3.16) in the standard phosphorylase phosphatase assay.

Phosphorylase (50 mM) is dialyzed extensively against NaF (15 mM) to block endogenous phosphatase activity. The protein is diluted to 3 mg/ml (30 pmol/$\mu$l) in Tris HCl (50 mM, pH 7.0) containing ethylenediamine tetra-acetic acid (EDTA, 0.1 mM), bovine serum albumin (1 mg/ml), 2-mercaptoethanol (0.2% v/v) and caffeine (15mM). An incubation comprising 10 $\mu$l protein phosphatase-1 or -2A (PP2A, 1 mU/ml in Tris HCl, pH 7.0) and 10 $\mu$l phosphatase inhibitor (in Tris HCl, pH 7.0) is carried out for 10 minutes at 30° C. An aliquot (10 $\mu$l) of phosphorylase (30 pmol/$\mu$l, specific radioactivity $>0.6\times10^6$ dpm/nmol) is added to start the reaction, which is terminated after 10 minutes by adding 200 $\mu$l trichloroacetic acid (20% w/v,TCA). The suspension is vortexed, stood on ice for 1 minute and centrifuged at 15,000g for 2 minutes. An aliquot (200 $\mu$l) of supernatant is added to 1 ml scintillant and counted. One milliunit(mU) of protein phosphatase activity releases 1 nmol phosphate from phosphorylase per minute. Thus, 10 $\mu$l of a 1 mU/ml solution of PP1/2A causes 33% dephosphorylation of phosphorylase a in 10 minutes in the standard assay, which is linear to this level of dephosphorylation.

Homogeneous PP-1 and -2A catalytic subunits are purified from rabbit skeletal muscle.

Radiolabelled phosphorylase a is prepared from phosphorylase b (Boehringer-Mannheim) by phosphorylation with $^{32}$P-$\gamma$-ATP (Amersham) and phosphorylase kinase (Sigma). Prior to use, phosphorylase kinase and phosphorylase b preparations are routinely preincubated with 25 nM NaF to inhibit endogenous phosphatase activity.

Using a standard commercial preparation of okadaic acid, the IC$_{50}$ for PP1 and PP2A inhibition is 19 nM and 0.2 nM, respectively, in the standard phosphorylase a phosphatase assay. The IC$_{50}$'s correspond to okadaic acid detection limits of 432 pg (PP1) and 4.8 pg (PP2A) per $\mu$l when an unknown sample is added to the enzyme assay.

Confirmatory identification of the toxin is obtained by inspection of relative PP1:PP2A inhibition ratios Okadaic acid inhibits PP2A 90($\pm$10)-fold more strongly than PP1.

When OA is replaced by anti-idiotypic antibody 1/59, it inhibits the phosphatase activity in a similar to OA way. The IC$_{50}$ for PP1 and PP2A are 1.2 $\mu$M and 175 $\mu$M respectively. The antibody is similar to OA in that it is more active against PP2A than PP1. However, the antibody is less active than OA as an inhibitor of pp2A and PP1 activities. This example confirms that anti-idiotypic antibody 1/59 behaves as OA in biological assay.

EXAMPLE IV

Quantitation of Okadaic Acid in a Competitive ELISA Based on the Competition Between Solid-phase Fixed Okadaic Acid and Free OA For Binding to 6/50 Antibody This assay is based on the competition between solid-phase attached OA and free OA (analyte) for binding to a limited number of binding sites on 6/50 IgG in solution.

Figure 5:
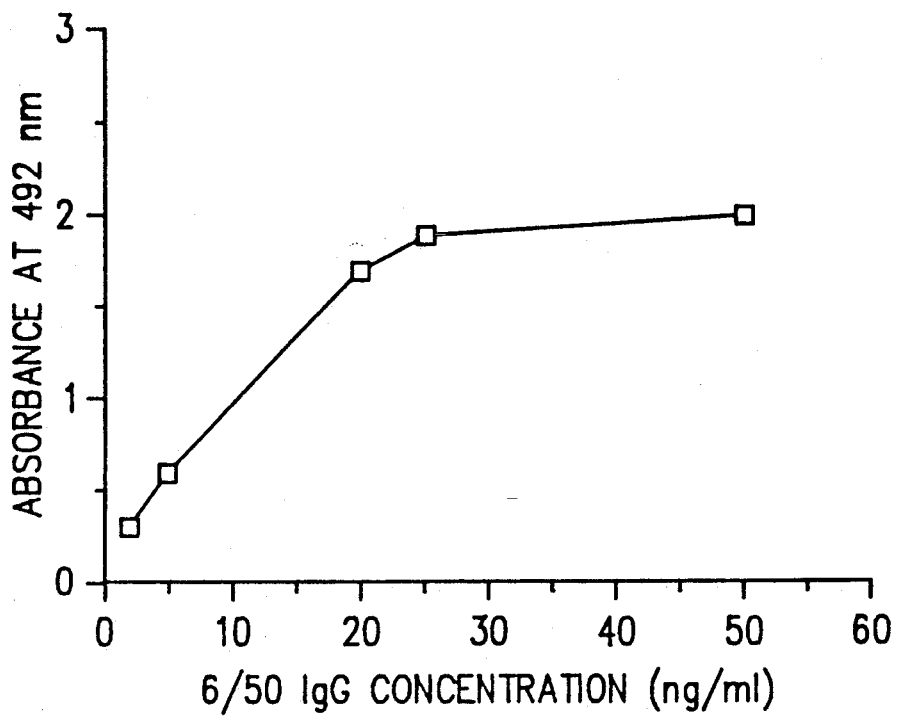
FIG. 5 shows a curve of the titration of 6/50 IgG in ELISA against okadaic acid.

To establish the limiting concentration of 6/50 IgG, the antibody titration curve is drawn (FIG. 5) and 50% of maximum binding calculated.

Thus, 96-well microtiter plates are coated with 100 $\mu$l of OA-OVAL (10 $\mu$g/ml) in 0.05M sodium carbonate bicarbonate buffer, pH 9.6, overnight at 4° C. The unbrund OA-OVAL is washed off with Tris-buffered saline and the remaining binding sites are saturated with 200 $\mu$l of TS-MILK for one hour at 37° C. After washing, the wells are incubated simultaneously with 50 $\mu$l of OA standards (0–30 ng/ml) diluted in 10% MeOH and applied in the presence of 50 $\mu$l of limiting amounts of 6/50 IgG for one hour at 37° C. After the unbound antibody and antigen are washed off, 100 $\mu$l of a peroxidase conjugated goat anti-mouse IgG antiserum diluted in TS-MILK is added and incubated for one hour at 37° C.

Figure 6:
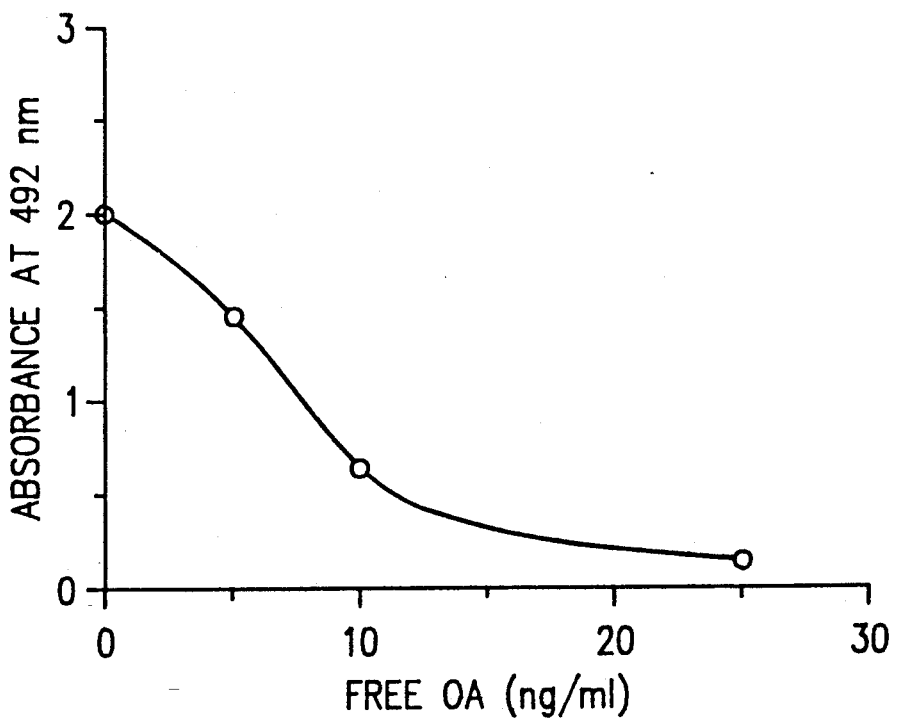
FIG. 6 shows a curve of the competition between solid-phase fixed okadaic acid and free okadaic acid for binding to 6/50 IgG in ELISA.

Ihe colorimetric reaction is developed upon the addition of 0.03% H$_2$O$_2$ in 0.1 M sodium citrate buffer, pH 7.0, containing 0.1% OPD. The reaction is stopped with 3 N H$_2$SO$_4$ and the color intensity measured at a wavelength of 492 nm using a BioRad ELISA reader. Under such conditions free OA competes with solid-phase fixed OA for binding to 6/50 in a dose-dependent manner, that is proportional to the amount of free OA present as illustrated in FIG. 6.

A standard curve of known amounts of OA has been established (FIG. 6) allowing for the detection of OA in the picogram to nanogram range. The curve is linear within 1–10 ng/ml range.

Figure 7:
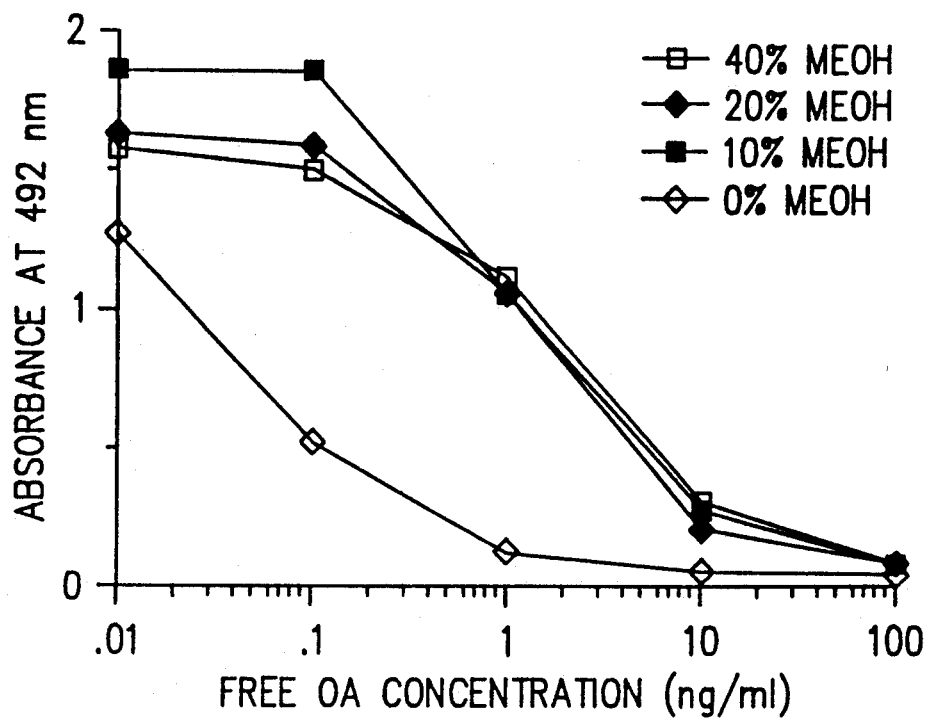
FIG. 7 shows a curve of the influence of methanol on 6/50 IgG binding to okadaic acid in a competition ELISA.

Since OA is only soluble in the presence of organic solvents, the influence of varying concentrations of methanol on the antigen-antibody reaction has been investigated. The results are presented in FIG. 7. It is obvious that methanol has a deleterious effect on 6/50 IgG binding to OA since the sensitivity of OA detection in the presence of 40% MeOH drops considerably when compared with 10% MeOH content. The addition of 10% MeOH seems to be the optimal for this assay. Absence of MeOH decreases OA solubility and thus the slope of the standard curve.

EXAMPLE V

Quantitation of OA in a Competitive ELISA Based on the Competition Between Solid-phase Fixed Anti-idiotypic Antibody 1/59 and Free OA For Binding to Anti-OA Antibody 6/50.

Idiotype-anti-Idiotype ELISA

Briefly, 96-well microtiter plates are coated with 100 $\mu$l of 10 $\mu$g/ml of F(ab')$_2$ fragments of 1/59 IgG in 0.05M sodium carbonate bicarbonate buffer, pH 9.6, overnight at 4° C. The unbound F(ab')$_2$ fragments are washed off with Tris-buffered saline and the remaining binding sites are saturated with 200 $\mu$l of TS-MILK for one hour at 37° C. After washing, the wells are incubated simultaneously with 50 $\mu$l of a fixed amount of anti-OA 6/50 IgG (30 ng/ml) and 50 μl of free OA diluted in 10% MeOH at increasing concentrations (0–100 ng/ml) for one hour at 37° C. After the unbound antibody is washed off with TS-Tween ® 100 μl of a peroxidase conjugated goat anti-mouse IgG Fc-fragment-specific antiserum diluted in TS-MILK is added and incubated for one hour at 37° C.

Figure 8:
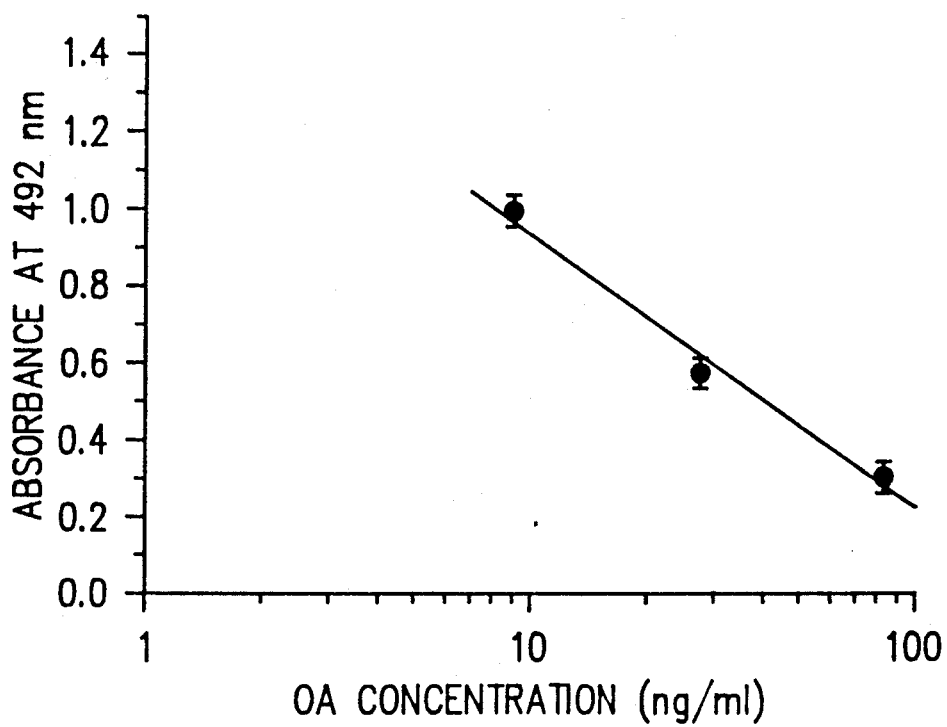
FIG. 8 shows a standard curve of the inhibition of anti-OA 6/50 IgG binding to F(ab')$_2$ fragment of anti-OA anti-idiotypic 1/59 IgG by free OA in ELISA.

The colorimetric reaction is developed upon the addition of 0.03% $H_2O_2$ in 0.1 M sodium citrate buffer, pH 7.0, containing 0.1% OPD. The reaction is stopped with 3 N $H_2SO_4$ and the color intensity measured at a wavelength of 492 nm using a BioRad ® ELISA reader. The obtained standard curve is presented in FIG. 8.

The assay is reliable, sensitive (5 ng/ml) and linear in the range of 9–81 ng OA/ml. It is simple, fast to perform and inexpensive, as 1/59 murine monoclonal antibody is available in unlimited quantities as hybridoma product. Clone is a good producer and antibody can be purified in a non-expensive way.

The cross-reactivity of 6/50 antibody with other related toxins is demonstrated in FIG. 9.

Figure 9A:
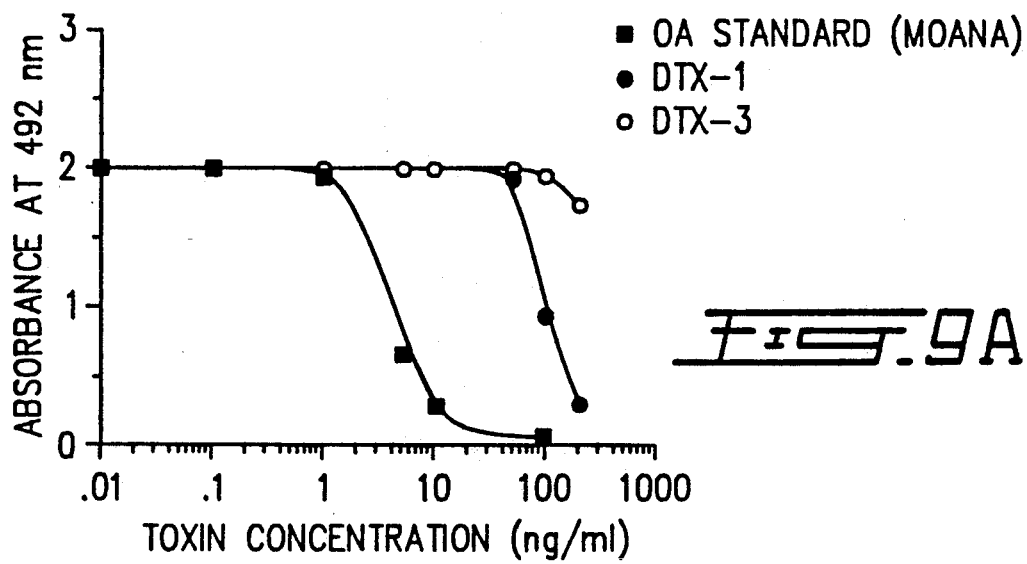
FIG. 9 shows the cross-reactivity of mAb 6/50 with OA, DTX-1, DTX-3 and various other analogues of FIG. 9A Assay wells were coated with OA and incubated with a fixed concentration of 6/50 IgG and varying amounts of each toxin in 40% MEOH.
FIG 9B & 9C Assay wells were coated with purified antiidiotypic antibody (1/59) F(ab')$_2$ fragments (5 μg/ml) and incubated with a fixed concentration of mAb 6/50 (100 ng/ml) and varying amounts of OA analogues in 40% MEOH.

In FIG. 9A, the assay wells were coated with OA and incubated with a fixed concentration of 6/50 IgG and varying amounts of each toxin in 40% MEOH. Bound antibody was detected with HRP-conjugated anti-mouse IgG. Toxins used in this competitive ELISA were generously donated by Dr. Takeshi Yasumoto (Tohoku University, Japan).

Figure 9B:
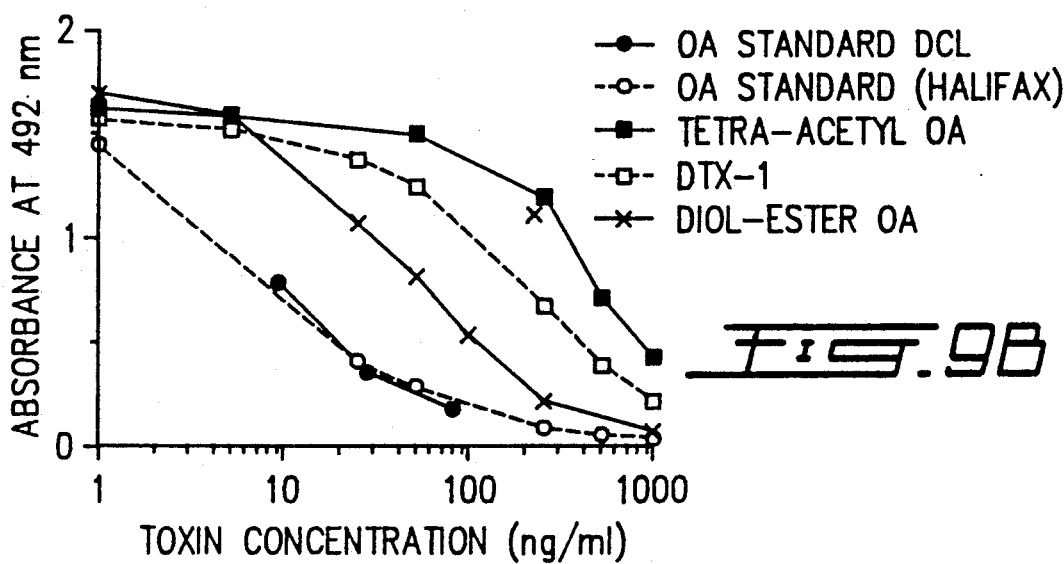
Figure 9C:
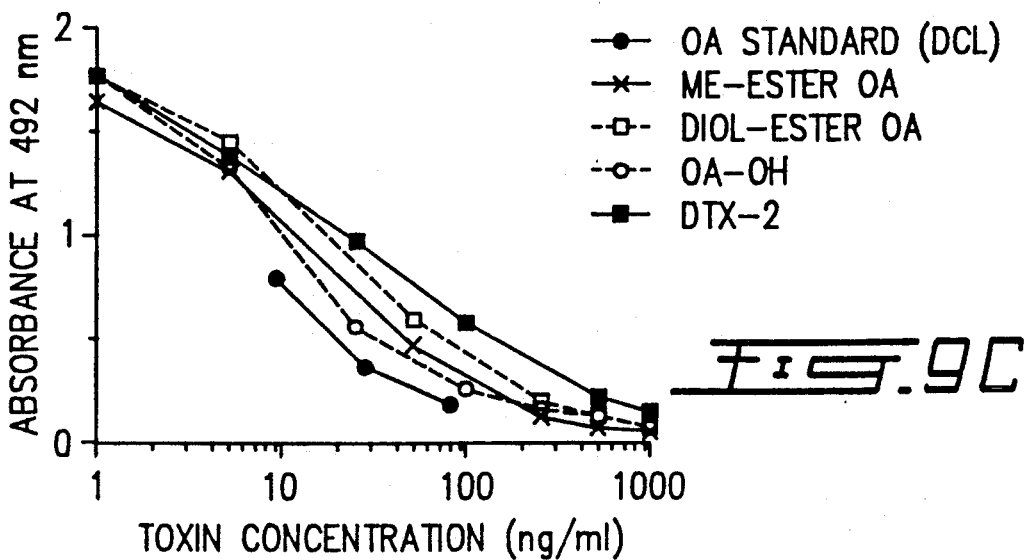
Figure 10:
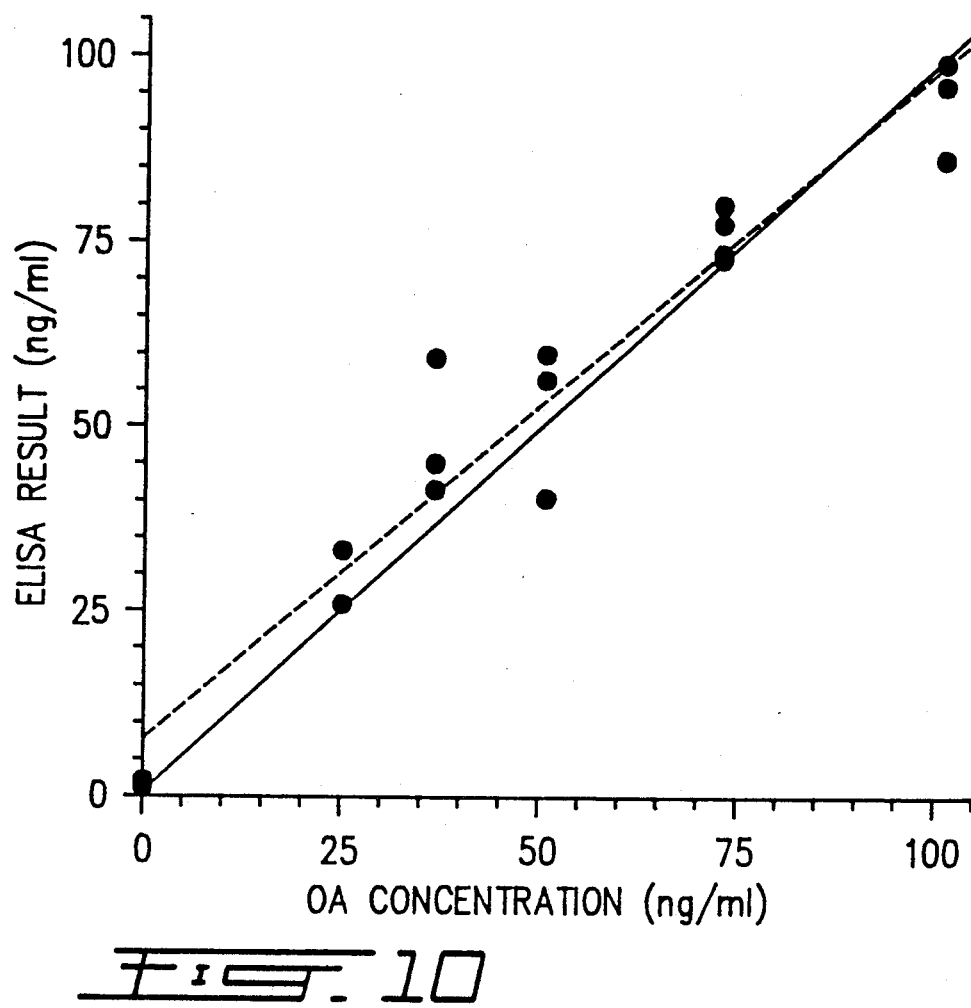
FIG. 10 compares the HPLC method with the claimed Idiotype-anti-Idiotype ELISA (Example V) for quantitation of OA in mussel samples.

For FIG. 9B and 9C, the assay wells were coated with purified anti-idiotypic (1/59) F(ab')$_2$ (5μg/ml) and incubated with a fixed concentration of antibody 6/50 (100 ng/ml) and varying amounts of okadaic acid analogues in 40% MEOH. Bound 6/50 IgG was detected with HRP-conjugated anti-mouse IgG Fc fragment specific antisera.

Figure 11:
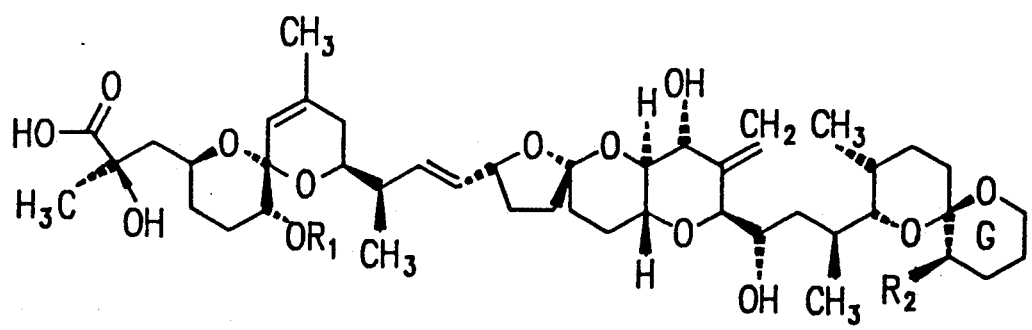
FIG. 11 shows the structure of okadaic acid and its derivatives.

The 6/50 antibody seems to recognize the G-ring side of the okadaic acid molecule (FIG. 11) but not the carboxyl side since all ester and hydroxyl derivatives of okadaic acid reacted as well as okadaic acid with 6/50 antibody while methyl okadaic acid (DTX-1), tetra acetyl okadaic acid and DTX-3 bound to 6/50 antibody with significantly lower affinity.

EXAMPLE VI

Preparation of Seafood For OA Extraction and Quantitation

Each gram of whole mussel is homogenized with 4 ml of aqueous 80% methanol for 2 minutes at room temperature using a kitchen blender. The homogenate is centrifuged at 3,000 RPM for 15 minutes. The supernatant is then stored at −20° C. until needed. Testing of a mussel from Holland prepared in the above manner has revealed that both competitive assays of Example: IV and V yielded quite accurate results (Table 2).

TABLE 2

| Sample | Assay IV OA-Id (ng/ml) | Assay V Id-anti-Id (ng/ml) |
|---|---|---|
| Holland mussel | 1,100 | 950 |

Id = idiotype

The assay IV in which true okadaic acid has competed with the solid-phase bound OA for limited binding sites on the 6/50 IgG detected 1,100 ng OA/ml in the Holland sample. The assay V in which solid-phase bound OA was replaced with $F(ab')_2$ derived from the 1/59 anti-idiotypic IgG has detected 950 ng OA/ml in the same sample. Furthermore, these results have been confirmed by PP1/PP2A inhibition assay.

Okadaic acid extracted from the same Holland mussel was also analyzed by HPLC using the method of Lee et al (AGRIC. BIOL. CHEM., 1987, 51, 877-881) and found to contain approximately 1,000 ng OA/ml. The sample was then diluted serially and tested in ELISA of Example V. FIG. 10 shows a good correlation between these two methods.

EXAMPLE VII

Spiking of Mussels With Okadaic Acid.

Two mussels were spiked with okadaic acid. Sample I (9.1 g wet tissue) was injected with 70 mg of OA in methanol and Sample II (6.7 g wet tissue) with 27 mg of OA. Both samples were then extracted with 80% methanol as described in Example VI and assayed in the ELISA of Example V. Concentrations of OA in those samples were interpolated from the OA standard curve (FIG. 8).

TABLE 3

Recovery of okadaic acid from spiked mussels by Idiotype-anti-Idiotype ELISA (Assay of Example V)

| | Okadaic acid found | | |
|---|---|---|---|
| Okadaic acid added (μg/g) | Average* (μg/g) | ±Standard deviation (μg/g) | Coefficient of variation |
| 7.7 (Sample I) | 8.48 | 0.8 | 9 |
| 4 (Sample II) | 4.04 | 0.64 | 15 |

*n = 10

The results are presented in Table 3 and indicate that 110% of OA was recovered from spiked mussel I and 100% from mussel II using the Idiotype-anti-Idiotype ELISA assay of Example V.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. An anti-idiotypic monoclonal antibody produced by the hybridoma ATCC HB 10768 and raised against a mouse monoclonal antibody produced by the hybridoma ATCC HB 10767 and specific to at least one diarrhetic shellfish poisoning toxin selected from the group consisting of okadaic acid and derivatives thereof, wherein said anti-idiotypic antibody is not immunoreactive with any non-anti-diarrhetic shellfish poisoning toxing antibody or fragments thereof, and wherein said anti-idiotypic antibody is an internal image of said diarrhetic shellfish poisoning toxin.

* * * * *

UNITED STATES PATENT AND TRADEMARK OFFICE
CERTIFICATE OF CORRECTION

PATENT NO. : 5,264,556  
DATED : November 23, 1993  
INVENTOR(S) : Hanna Sikorska, et al Page 1 of 6

It is certified that error appears in the above-indentified patent and that said Letters Patent is hereby corrected as shown below:

```
Column 2, line 45, after "provided" insert a comma [,];
          line 64, after "thereof" insert a period [.];
Column 3, line 25, after "obtained" insert a period [.];
          line 33, change "antiidiotypic" to
--anti-idiotypic--;
Column 4, line 13, after "of" insert --OA.--;
          line 18, change "antiidiotypic" to
--anti-idiotypic--;
          line 33, after "antibody" insert a period [.];
Column 5,
          line 66, after "enzymes" insert a period [.];
          line 66, change "4" to --4.-- and begin a new
paragraph;
Column 6, line 51, after "Immunogen" insert a period [.];
          line 57, change "bodiimice" to --bodiimide--;
          line 63, after "4° C" delete the period [.];
```

UNITED STATES PATENT AND TRADEMARK OFFICE
CERTIFICATE OF CORRECTION

PATENT NO. : 5,264,556
DATED : November 23, 1993
INVENTOR(S) : Hanna Sikorska, et al It is certified that error appears in the above-indentified patent and that said Letters Patent is hereby corrected as shown below:

Column 7, line 22, change "P3X63,Ag8.653," to --P3X63.Ag8.653,--;
        line 26, change "$2X10^{-3}M$" to --$2X10^{-3}$ M--;
        line 27, change "$5X10^{-2}M$" to --$5X10^{-2}$ M--;

line 44, change "Dubelcco's" to --Dulbecco's--;
        line 64, change "$1X10^{-4}M$" to --$1X10^{-4}$ M--;
        line 67, change "con-centration" to --concentration--;

Column 8, line 7, change "e-ual" to --equal--;
        line 28, change "0.1M" to --0.1 M--;
        line 41, change "IMDM-$1X10^{-4}M$" to --IMDM-$1X10^{-4}$ M--;
        line 41, change "$1.6X10^{-5}M$" to --$1.6X10^{-5}$ M--;
        line 48, change "-haracterization" to --characterization--;
        line 63, delete the period [.] after "-20° C";

UNITED STATES PATENT AND TRADEMARK OFFICE
CERTIFICATE OF CORRECTION

PATENT NO. : 5,264,556
DATED : November 23, 1993
INVENTOR(S) : Hanna Sikorska, et al It is certified that error appears in the above-indentified patent and that said Letters Patent is hereby corrected as shown below:

Column 9, line 12, change "Tne" to --The--;

line 17, change "immunoglooulin" to --immunoglobulin--;

line 18, delete the period [.] after "-20° C";

line 50, change "0.1M" to --0.1 M--;

line 51, change "Unigested" to --undigested--;

line 55, change "IqG" to --IgG--;

line 57, change "minec" to --mined--;

line 65, change "12.301" to --12301--;

line 66, change "Jun." to --June--;

Column 10, line 5, change "monoclonal" to --Monoclonal--;

lines 7-11, delete in their entirety and insert therefor -- 1. Preparation of Immunogen. Conjugation of Anti-okadaic Acid Monoclonal Anti-body (6/50) to Tuberculin Purified Protein Derivatives (PPD)--;

line 26, delete the period after "-20° C";

UNITED STATES PATENT AND TRADEMARK OFFICE
CERTIFICATE OF CORRECTION

PATENT NO. : 5,264,556
DATED : November 23, 1993
INVENTOR(S) : Hanna Sikorska et al.

It is certified that error appears in the above-indentified patent and that said Letters Patent is hereby corrected as shown below:

Column 10, line 33, change "anti-body-PPD" to --antibody-PPD--;

line 52, change "Hyoridoma" to --Hybridoma--;

line 62, change "(Ab2)" to --($Ab_2$)--;

Column 11, line 8, change "106" to --$10^6$--;

line 19, change "furtner" to --further--;

line 22, change "rurther" to --further--;

line 32, delete the period [.] after "-20° C";

line 33, change "Immunoqlobulin" to --Immunoglobulin--;

line 40, change "$\mu$mmunoglobulin" to --immunoglobulin--;

line 49, delete the period [.] after "C";

line 50, change "1M" to --1 M--;

Column 12, line 42, change "0.05M" to --0.05 M--;

Column 13, line 24, change "106" to --$10^6$--;

line 28, change "15,000g" to --15,000 g--;

UNITED STATES PATENT AND TRADEMARK OFFICE
CERTIFICATE OF CORRECTION

PATENT NO. : 5,264,556
DATED : November 23, 1993
INVENTOR(S) : Hanna Sikorska et al.

It is certified that error appears in the above-indentified patent and that said Letters Patent is hereby corrected as shown below:

Column 13, line 30, change "milliunit(mU)" to --milliunit (mU)--;
line 56, insert a period [.] after "ratios";
line 65, change "pp2A" to --PP2A--;
Column 14, line 16, change "0.05M" to --0.05 M--;
line 18, change "brund" to --bound--;
line 29, change "Ihe" to --The--;
lines 29-30, change "add:-tion" to --addition--;
line 45, change "invastigated" to --investigated--;
line 63, change "0.05M" to --0.05 M--;

UNITED STATES PATENT AND TRADEMARK OFFICE
CERTIFICATE OF CORRECTION

PATENT NO.  : 5,264,556
DATED       : November 23, 1993
INVENTOR(S) : Hanna Sikorska et al.

It is certified that error appears in the above-indentified patent and that said Letters Patent is hereby corrected as shown below:

```
Column 15, line  3, change "unbcund" to --unbound--;
          line 24, change "MEOH" to --MeOH--;
          line 33, change "MEOH" to --MeOH--;
          line 51, delete the period [.] after "20° C";
          line 53, change "Example:" to --Examples--;
Column 16, line  9, change "al" to --al.--; and
          line 61, change "toxing" to --toxin--.
```

Signed and Sealed this

Eighth Day of November, 1994

BRUCE LEHMAN

*Attest:*

*Attesting Officer*    *Commissioner of Patents and Trademarks*